(12) United States Patent
Kim et al.

(10) Patent No.: US 10,408,825 B2
(45) Date of Patent: Sep. 10, 2019

(54) BIOSENSOR

(71) Applicant: ELECTRONICS AND TELECOMMUNICATIONS RESEARCH INSTITUTE, Daejeon (KR)

(72) Inventors: Young Jun Kim, Daejeon (KR); Wan Joong Kim, Daejeon (KR); Bong Kyu Kim, Daejeon (KR); Kwang Hyo Chung, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 376 days.

(21) Appl. No.: 15/158,364

(22) Filed: May 18, 2016

(65) Prior Publication Data

US 2016/0341724 A1    Nov. 24, 2016

(30) Foreign Application Priority Data

May 19, 2015  (KR) .................. 10-2015-0069920
Mar. 31, 2016  (KR) .................. 10-2016-0038919

(51) Int. Cl.
*G01N 33/543*  (2006.01)
*G01N 21/78*  (2006.01)
*B01L 3/00*  (2006.01)

(52) U.S. Cl.
CPC ...... *G01N 33/54366* (2013.01); *B01L 3/5027* (2013.01); *G01N 21/78* (2013.01); *B01L 2200/16* (2013.01); *B01L 2300/0636* (2013.01); *B01L 2300/0838* (2013.01);
(Continued)

(58) Field of Classification Search
None
See application file for complete search history.

(56) References Cited

U.S. PATENT DOCUMENTS 4,690,907 A * 9/1987 Hibino ................. G01N 33/558
                                                    422/417
4,918,025 A * 4/1990 Grenner ............... B01L 3/5027
                                                    422/565
(Continued)

FOREIGN PATENT DOCUMENTS

CN  102998472 A    3/2013
JP  2001-521148 A  11/2001
(Continued)

OTHER PUBLICATIONS

Yuan-Cheng Cao, "A Capillary Based Chemiluminscent Multi-Target Immunoassay", Mar. 4, 2015, pp. 563-568, vol. 25, Springer Science+Business Media, New York, USA.
(Continued)

*Primary Examiner* — Christopher L Chin (57) ABSTRACT

Disclosed is a biosensor, comprising: a sensor part including a capillary chip configured to detect a target material; and a pre-treatment part connected to the sensor part and configured to provide a mixed solution including a substrate to the sensor part, in which the capillary chip includes a capillary, at least one of antibody for antigen-antibody reaction with the target material inside the capillary, and a photo sensor detecting a color of the substrate.

14 Claims, 8 Drawing Sheets

(52) U.S. Cl.
CPC .................. *B01L 2300/0867* (2013.01); *B01L 2400/0478* (2013.01); *C12Y 111/01007* (2013.01)

(56) References Cited

U.S. PATENT DOCUMENTS

| | | | | |
|---|---|---|---|---|
| 5,474,902 | A * | 12/1995 | Uylen | G01N 33/54366 422/503 |
| 5,637,467 | A * | 6/1997 | Meltzer | G01N 33/528 435/188 |
| 6,020,209 | A * | 2/2000 | Narang | G01N 33/54366 422/504 |
| 6,221,624 | B1 * | 4/2001 | Lihme | G01N 33/535 435/28 |
| 7,708,944 | B1 * | 5/2010 | Sadik | G01N 33/5302 422/412 |
| 7,935,489 | B2 * | 5/2011 | O'Neill | B01L 3/502715 422/422 |
| 8,414,844 | B2 * | 4/2013 | Sadik | G01N 33/5302 422/400 |
| 10,168,266 | B2 * | 1/2019 | Kim | G01N 11/04 |
| 2004/0029177 | A1 | 2/2004 | Nadaoka et al. | |
| 2010/0133510 | A1 | 6/2010 | Kim et al. | |
| 2010/0134799 | A1 | 6/2010 | Huh et al. | |
| 2012/0142017 | A1 * | 6/2012 | Park | G01N 33/54366 435/7.1 |
| 2012/0225491 | A1 | 9/2012 | Ram et al. | |
| 2015/0118695 | A1 | 4/2015 | Paek | |
| 2015/0160203 | A1 | 6/2015 | Choi et al. | |
| 2018/0188238 | A1 * | 7/2018 | Kim | G01N 33/52 |

FOREIGN PATENT DOCUMENTS

| | | |
|---|---|---|
| JP | 2013-076642 A | 4/2013 |
| KR | 10-0550707 B1 | 2/2006 |
| KR | 10-1280054 B1 | 6/2013 |
| KR | 10-2015-0048381 A | 5/2015 |

OTHER PUBLICATIONS

A. Xiang et al., "A simple and rapid capillary chemiluminescence immunoassay for quantitatively detecting human serum HBsAg", Jun. 19, 2013, pp. 1-8, vol. 32, Springer.

* cited by examiner

BIOSENSOR

CROSS-REFERENCE TO RELATED APPLICATION

The present application claims priority to Korean Patent Application Numbers 10-2015-0069920 filed on May 19, 2015 and 10-2016-0038919 filed on Mar. 31, 2016, in the Korean Intellectual Property Office, the entire disclosures of which are incorporated by reference herein in their entirety.

BACKGROUND

1. Field

The present disclosure relates to a biosensor, and more particularly, to a portable biosensor.

2. Description of the Related Art

An immunoassay is an analysis method based on an antigen-antibody interaction, and is a method of quantifying organic materials by mainly using the organic materials as an analysis target. The representative form of the immunoassay is an Enzyme-Linked Immunosorbent Assay (ELISA), in which various samples may be simultaneously measured. However, there is a problem in that a phased analysis process is still required, and time, manpower, professional level knowledge, and a laboratory level device for measuring a signal are required.

Further, various biosensors implemented in a strip scheme have been recently developed, but since reproducibility or accuracy is low and a manipulation in various stages is required, there is inconvenience in that it is not that anybody can easily use the biosensor.

SUMMARY OF THE INVENTION

The present disclosure has been made in an effort to solve the above-described problems associated with the prior art, and provides a biosensor having more improved accuracy and reproducibility than those of the related art. The present disclosure has also been made in an effort to solve the above-described problems associated with the prior art, and provides a one-touch type biosensor which a user may easily use.

The present disclosure has also been made in an effort to solve the above-described problems associated with the prior art, and provides a method of manufacturing the biosensor.

An exemplary embodiment of the present disclosure provides a biosensor, comprising: a sensor part including a capillary chip configured to detect a target material; and a pre-treatment part connected to the sensor part and configured to provide a mixed solution including a substrate to the sensor part, in which the capillary chip includes a capillary, at least one of antibody for antigen-antibody reaction with the target material inside the capillary, and a photo sensor detecting whether the substrate develops a color.

The sensor part may include: a capillary having a first region and a second region connected to the first region; a chromogenic enzyme-detection antibody provided onto an inner wall of the capillary in the first region; and a capture antibody fixed onto the inner wall of the capillary in the second region and configured to capture the target material.

The sensor part may include: a capillary having a first region and a second region connected to the first region; a chromogenic enzyme-target material provided onto an inner wall of the capillary in the first region; and a capture antibody fixed onto the inner wall of the capillary in the second region and configured to capture the target material. The target antibody may be competitively bonded with the target material and the chromogenic enzyme-target material.

The sensor part may include: a capillary having a first region and a second region connected to the first region; a chromogenic enzyme-detection antibody provided onto an inner wall of the capillary in the first region; and a target material-carrier complex provided on an inner wall of the capillary in the second region. The carrier may be bovine serum albumin or casein.

The mixed solution may include the substrate and a washing solution. The substrate may be any one of TMB(3,3',5,5'-Tetramethylbenzidine), and DAB(3,3'-Diaminobenzidine), ABTS(2,2'-azino-bis(3-ethylbenzothiazoline-6-sulphonic acid)). The mixed solution may further include an oxidizer, and the chromogenic enzyme may be horseradish peroxidase, and the substrate may be the TMB.

The photo sensor may detect transmittance according to whether the substrate develops a color.

The capillary chip may be mounted to and detached from the pre-treatment part.

The pre-treatment part may include the mixed solution, a container accommodating the mixed solution, and a mixed solution providing means providing the mixed solution to the capillary chip, and the mixed solution providing means may be a piston.

The biosensor may further include a calculation part connected to the sensor part and the pre-treatment part, and configured to control the sensor part and the pre-treatment part, and calculate a result by the sensor part. The calculation part may include a display outputting the result, or may output the result to a wirelessly connected external device.

Another exemplary embodiment of the present disclosure provides a method of manufacturing a biosensor, including: preparing a sensor part; manufacturing a pre-treatment part; and connecting the sensor part and the pre-treatment part, in which wherein the manufacturing of the pre-treatment part includes: manufacturing a capillary; disposing at least one of antibody within the capillary; and disposing a photo sensor at least one side of the capillary.

The disposing of at least one of antibody within the capillary may include: disposing a chromogenic enzyme-detection antibody in a first region of the capillary; and fixing a capture antibody to a second region of the capillary.

The disposing of at least one of antibody within the capillary may include: disposing a chromogenic enzyme-target material in a first region of the capillary; and fixing a capture antibody to a second region of the capillary.

The capture antibody may be freeze-dried.

The disposing of at least one of antibody within the capillary may include: disposing a chromogenic enzyme-detection antibody in a first region of the capillary; and fixing a target material-carrier to a second region of the capillary.

The present disclosure provides the one-touch biosensor, of which a manufacturing method and a usage method are simple. The biosensor adopts the ELISA, thereby increasing accuracy and reproducibility.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

DETAILED DESCRIPTION OF THE INVENTION

The present disclosure may be variously modified and have various forms, so that specific exemplary embodiments will be illustrated in the drawings and described in detail in the text. However it should be understood that the invention is not limited to the specific embodiments, but includes all changes, equivalents, or alternatives which are included in the spirit and technical scope of the present disclosure.

In the description of respective drawings, similar reference numerals designate similar elements. In the accompanying drawings, sizes of structures are illustrated to be enlarged compared to actual sizes for clarity of the present disclosure. Terms "first", "second", and the like may be used for describing various constituent elements, but the constituent elements should not be limited to the terms. The terms are used only to discriminate one constituent element from another constituent element. For example, a first element could be termed a second element, and similarly, a second element could be also termed a first element without departing from the scope of the present disclosure. As used herein, the singular forms are intended to include the plural forms as well, unless the context clearly indicates otherwise.

In the present disclosure, it should be understood that terms "include" or "have" indicates that a feature, a number, a step, an operation, a component, a part or the combination thoseof described in the specification is present, but do not exclude a possibility of presence or addition of one or more other features, numbers, steps, operations, components, parts or combinations, in advance. It will be understood that when an element such as a layer, film, region, or substrate is referred to as being "on" another element, it can be directly on the other element or intervening elements may also be present. Further, in the present disclosure, when a part of a layer, a film, an area, a plate, and the like is formed on another part, a direction, in which the part is formed, is not limited only to an up direction, and includes a lateral direction or a down direction. On the contrary, it will be understood that when an element such as a layer, film, region, or substrate is referred to as being "beneath" another element, it can be directly beneath the other element or intervening elements may also be present.

Hereinafter, an exemplary embodiment of the present disclosure will be described in detail in more detail with reference to the accompanying drawings.

Figure 1:
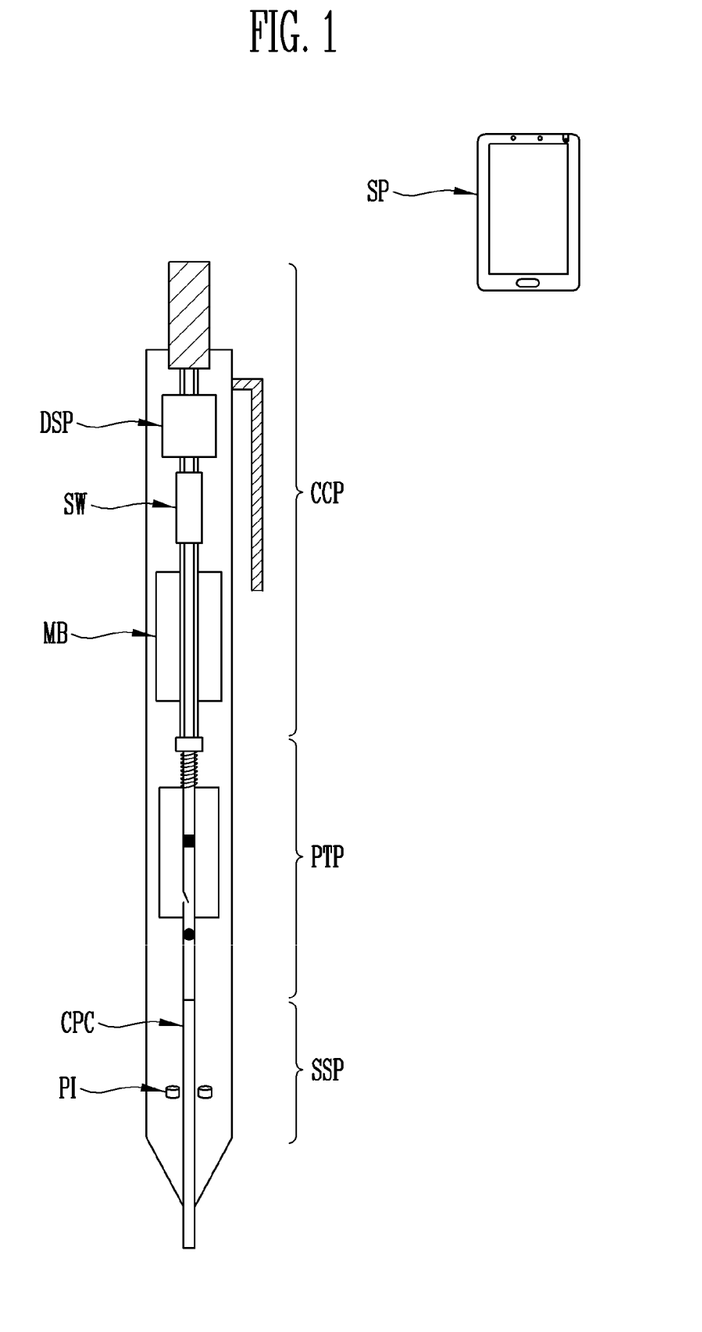
FIG. 1 is a diagram illustrating a biosensor according to an exemplary embodiment of the present disclosure.
Figure 2:
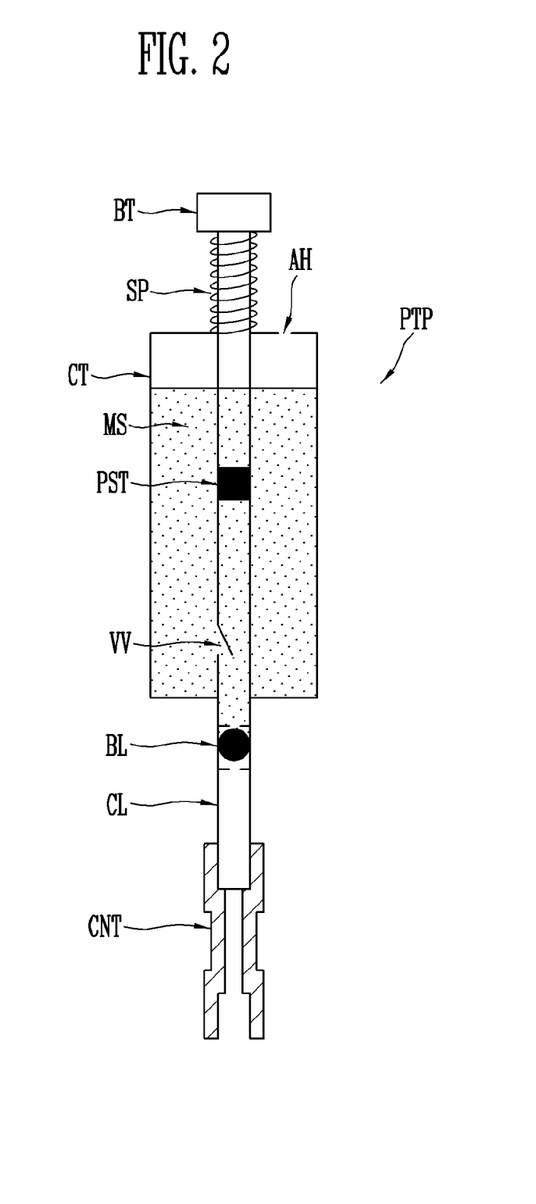
FIG. 2 is a diagram illustrating a pre-treatment part of FIG. 1.

FIG. 1 is a diagram illustrating a biosensor according to an exemplary embodiment of the present disclosure. FIG. 2 is a diagram illustrating a pre-treatment part PTP of FIG. 1, and FIG. 3 is a diagram illustrating a sensor part SSP of FIG. 1.

Figure 3:
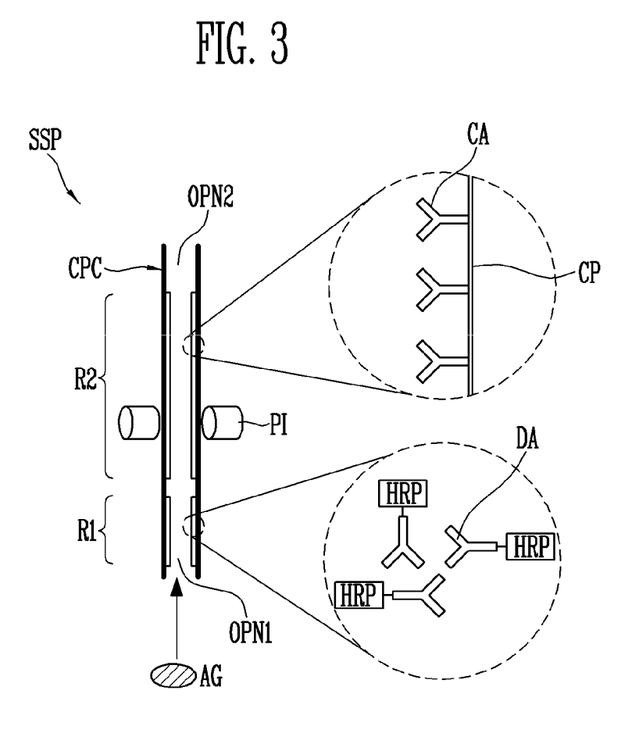
FIG. 3 is a diagram illustrating a sensor part of FIG. 1.

Referring to FIGS. 1 to 3, the biosensor according to the exemplary embodiment of the present disclosure includes the sensor part SSP to detect a target material, the pre-treatment part PTP to provide a mixed solution MS to the sensor part SSP, and a calculation part CCP to calculate a detecting result of the sensor part SSP.

The sensor part SSP is a part which detects a target material and draws a result such as a degree of color development.

The target material may be a biomarker, and particularly, a stress marker specific to stress. The biomarker may be protein, deoxyribonucleic acid (DNA), ribonucleic acid (RNA), metabolite, and the like, and it is possible to recognize existence of a specific material by detecting the biomarker.

In the exemplary embodiment of the present disclosure, the target material has an antigen-antibody specificity so as to act as an antigen AG Hereinafter, the target material is referred to as a target antigen AG The sensor part SSP includes a capillary chip CPC which is reacts with the target antigen AG and develops a color, and a photo sensor PI to detect a degree of color development in the capillary chip CPC.

The capillary chip CPC may include a material which exerts a specific antigen-antibody reaction with the target antigen AG, and includes a capillary CP, a chromogenic enzyme-detecting antibody HRP-DA, and a capture antibody CA.

The capillary CP is elongated in a direction, and has openings at both ends thereof. In the capillary CP, one end is an inlet (hereinafter, referred to as a "first opening OPN1") through which the target antigen AG flows into the capillary CP, and the other end is an inlet (hereinafter, referred to as a "second opening OPN2") through which a mixed solution to be described below flows into the capillary CP.

The capillary CP may include various materials, such as glass, crystal, and a transparent polymer. The polymer may include polystyrene, polymethyl methacrylate, poly dimethyl siloxane, polycarbonate, cyclic olefin copolymer, and the like.

A shape, a length, an inner diameter, and the like of the capillary CP are not particularly limited. According to the exemplary embodiment of the present disclosure, the capillary CP may be in straight shape with its longitudinal length covers from 10 mm to 100 mm. The capillary CP may also have various shapes in a cross-sectional view. For example, the capillary CP may have a shape of a circle, an ellipse, a polygon, etc.

Figure 4A:
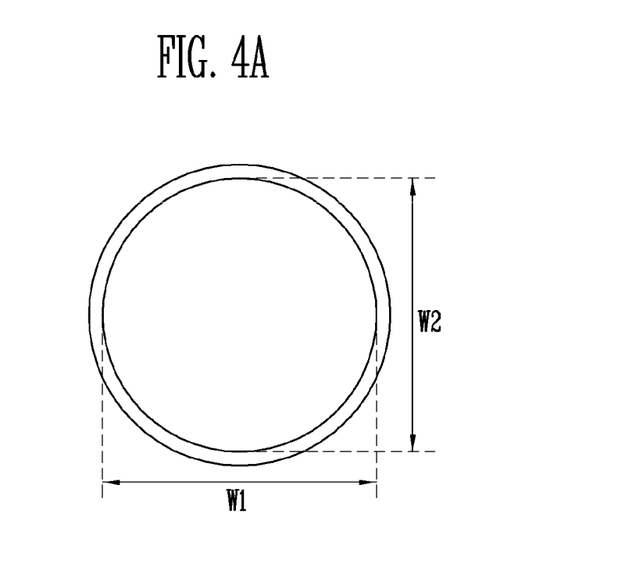
FIGS. 4A to 4E are cross-sectional views illustrating cross-sections of a capillary according to an exemplary embodiment of the present disclosure.
Figure 4B:
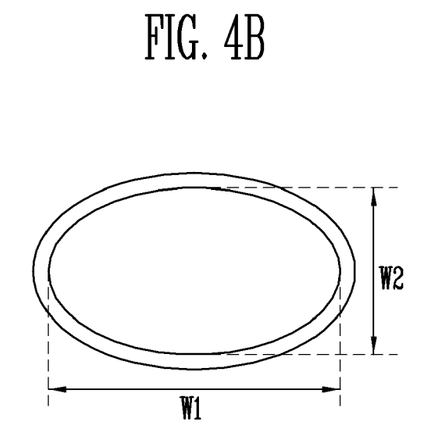
Figure 4C:
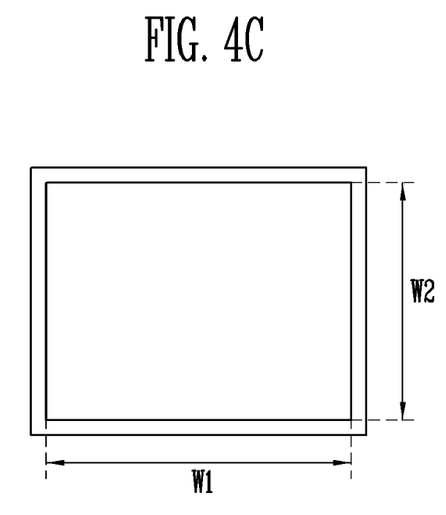
Figure 4D:
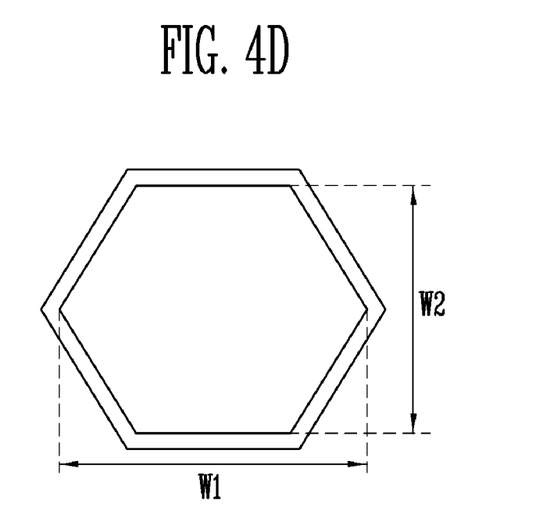
Figure 4E:
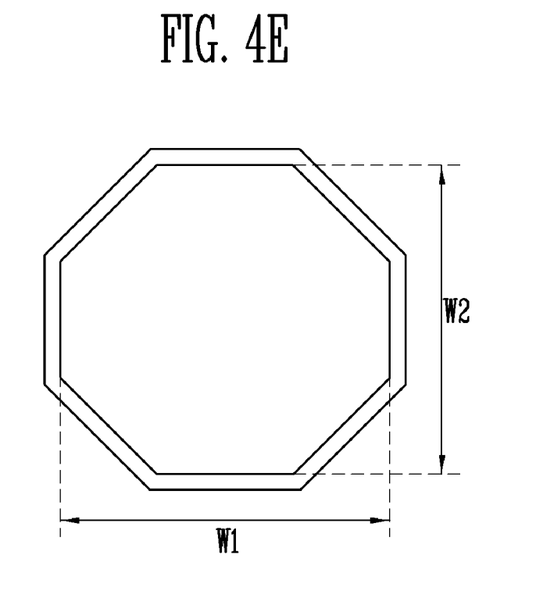

FIGS. 4A to 4E are cross-sectional views illustrating cross-sections of the capillary according to the exemplary embodiment of the present disclosure, and FIG. 4A illustrates a circular cross-section of the capillary, FIG. 4B illustrates an elliptical cross-section of the capillary, FIG. 4C illustrates a quadrangular cross-section of the capillary, FIG. 4D illustrates a hexagonal cross-section of the capillary, and FIG. 4E illustrates an octagonal cross-section of the capillary.

Referring to FIGS. 4A to 4E, the capillary according to the exemplary embodiment of the present disclosure may have a first width W1 in a first direction, and a second width W2 in a second direction vertical to the first direction. The first width W1 and the second width W2 may have various values according to the form of the capillary. For example, in FIG. 4A, the capillary is provided in a circular shape, so that the first width W1 and the second width W2 have the same value, that is, the same diameter. The diameter may be about 0.5 μm to about 900 μm. In FIG. 4B, the first width W1 and the second width W2 of the capillary have different values, and may be set within a range of about 0.5 μm to about 900 μm. In FIG. 4C, the first width W1 and the second width W2 of the capillary may have the same value or different values, and may be set within a range of about 0.5 μm to about 900 μm. In FIG. 4D, the first width W1 and the second width W2 of the capillary may have the same value or different values, and may be set within a range of about 0.5 μm to about 900 μm. In FIG. 4E, the first width W1 and the second width W2 of the capillary may have the same value or different values, and may be set within a range of about 0.5 μm to about 900 μm.

Further, in the exemplary embodiment of the present disclosure, the capillary CP may have a length of about 25 mm to about 40 mm, and may have an outer diameter of about 0.7 mm to about 1.1 mm. Here, the first width W1 and the second width W2 may be about 0.3 to about 0.6 mm. In another exemplary embodiment of the present disclosure, the capillary CP may have a length of about 30 mm to about 35 mm, and may have an outer diameter of about 0.8 mm to about 1.0 mm. Here, the first width W1 and the second width W2 may be about 0.4 mm to about 0.45 mm. In yet another exemplary embodiment of the present disclosure, the capillary CP may have a length of about 32 mm, and may have an outer diameter of about 0.89 mm. Here, the first width W1 and the second width W2 may be about 0.43 mm. In this case, a volume providable within the capillary CP corresponds to about 5 μm.

Referring back to FIGS. 1 to 3, the capillary CP has a first region R1 and a second region R2.

The first region R1 is a region close to the first opening OPN1 of the capillary CP, and the second region R2 is a region far from the first opening OPN1 and is close to the second opening OPN2.

The chromogenic enzyme-detecting antibody HRP-DA is provided on an inner wall corresponding to the first region R1 of the capillary CP. The chromogenic enzyme-detecting antibody HRP-DA may be freeze-dried and disposed in the first region R1 of the capillary CP.

The "chromogenic enzyme-detecting antibody HRP-DA" is a detection antibody DA complex, in which chromogenic enzyme (HRP) is labelled, and the detection antibody DA has an antigen-antibody specificity to the target antigen AG.

The chromogenic enzyme HRP may be horseradish peroxidase. The chromogenic enzyme HRP serves as a catalyst when the substrate is oxidized by using hydrogen peroxide as an oxidizer, and makes a substrate be developed with a specific color. The substrate with which the horseradish peroxidase reacts as a catalyst may include TMB(3,3',5,5'-Tetramethylbenzidine), DAB(3,3'-Diaminobenzidine), ABTS(2,2'-azino-bis(3-ethylbenzothiazoline-6-sulphonic acid)), but is not limited thereto.

In the exemplary embodiment of the present disclosure, the TMB may be used as the substrate.

The detection antibody DA may be selected from the antibodies having the antigen-antibody specificity to the target antigen AG The capture antibody CA is provided on an inner wall corresponding to the second region R2 of the capillary CP.

The capture antibody CA is an antibody having the antigen-antibody specificity to the target antigen AG and is fixed onto the inner wall of the second region R2. The capture antibody CA reacts with the target antigen AG, so that there is an effect in that the target antigen AG is fixed to the capture antibody CA.

The photo sensor PI is provided in the second region R2.

The photo sensor PI is provided to be adjacent to the capillary CP of the second region R2, and serves to detect whether the material within the capillary CP develops a color. Particularly, the photo sensor PI detects whether a color is developed and a degree of color development according to whether the chromogenic enzyme HRP within the second region R2 reacts with the substrate.

As long as the photo sensor PI is capable of detecting whether the material within the capillary CP develops a color, the kind of photo sensor is not limited, and the photo sensor PI may be implemented in various forms.

In the exemplary embodiment of the present disclosure, the photo sensor PI may be a transmissive photo sensor, and may include a light emitting element and a light receiving element with the capillary CP interposed therebetween. The photo sensor PI detects transmissive light in a form, in which the light receiving element receives light emitted from the light emitting element. A light emitting diode, such as GaAs and a GaAsP, a neon tube, a tungsten lamp, and the like may be used as the light emitting element, and a photo diode, a photo transistor, a CdS cell, and the like may be used as the light receiving element.

The photo sensor PI may be connected with a calculation part CCP to be described below, and a detection result of the photo sensor PI may be transmitted to the calculation part CCP later.

One side of the sensor part SSP having the aforementioned structure, particularly, the second opening OPN2 side in the capillary chip CPC, is connected with the pre-treatment part PTP.

The pre-treatment part PTP is a part for providing the mixed solution SM to the capillary chip CPC. The pre-treatment part PTP is connected to the second opening OPN2 of the capillary chip CPC.

The pre-treatment part PTP includes a container CT storing and accommodating the mixed solution MS, a mixed solution (MS) providing means, and the mixed solution MS included in the MS providing means.

The container CT accommodates the mixed solution MS to be provided to the capillary chip CPC inside thereof. The container CT may be provided in a cylindrical shape, but a shape thereof is not limited, and the container CT may be provided in various shapes, such as a spherical shape. In the exemplary embodiment of the present disclosure, an air hole AH for easily providing the mixed solution M to the capillary chip CPC may be provided at a part of the container CT.

The mixed solution MS may be a mixture of a substrate reacting with the chromogenic enzyme HRP and a washing solution washing an inner side of the capillary chip CPC.

Accordingly, the mixed solution MS reacts the chromogenic enzyme HRP and serves to wash the capillary CP.

In the mixed solution MS, the substrate may be the TMB, but is not limited thereto. In another exemplary embodiment of the present disclosure, the substrate may include DAB (3,3'-Diaminobenzidine), ABTS(2,2'-azino-bis(3-ethylbenzothiazoline-6-sulphonic acid)), but other publicly known substrates may be used as the substrate. In the mixed solution MS, hydrogen peroxide may be further included in the substrate. The TMB substrate is oxidized by hydrogen peroxide while HRP working as an enzyme.

As long as the washing solution is a stable solvent, which does not react with the substrate and other elements, the washing solution is not particularly limited.

The quantity of mixed solution MS provided to the capillary chip CPC one time or more may be accommodated in the container CT. In the exemplary embodiment of the present disclosure, the mixed solution MS having the quantity provided to the capillary CP several times may be accommodated in the container CT, and thus, the mixed solution MS may be provided to the capillary chip CP over several times.

The MS providing means is connected to the container CT. The MS providing means provides the mixed solution MS to the capillary chip CP, and a shape thereof is not particularly limited. In the exemplary embodiment of the present disclosure, the MS providing means may have a structure similar to that of a disposable syringe in order to provide the mixed solution MS to the sensor part SSP by a simple method (for example, one touch).

The MS providing means may include a cylinder CL, a piston PST, a button BT, a back flow preventing valve VV, a back flow preventing ball, and a connector CNT.

The cylinder CL accommodates the mixed solution MS inside thereof, and is connected to the capillary chip CPC by the connector CNT. The connector CNT connects the second opening OPN2 of the capillary chip CPC with one end of the cylinder CL, and may be formed of a material, such as silicon rubber. As long as the connector CNT is capable of connecting the capillary chip CPC with the cylinder CL, the connector CNT is not particularly limited.

The piston PST and the button BT for pressing the piston PST are provided at the other end side of the cylinder CL. The piston PST is disposed within the cylinder CL, and serves to push the mixed solution MS toward the capillary CP. The button BT is for the purpose of pressing the piston PST. The spring SP is for the purpose of restoring the piston PST to an original position after the button BT is pressed, and may be provided in a form surrounding the piston PST. The cylinder CL may be provided with the back flow preventing valve VV, which is opened when the piston PST is restored to the original position by the spring SP. The back flow preventing ball BL prevents a back flow when the mixed solution MS is reloaded by the button BT.

The pre-treatment part PTP having the aforementioned structure simply provides the mixed solution MS to the capillary chip CPC by pressing the button, that is, one touch.

In the exemplary embodiment of the present disclosure, the number of times of pressing the button BT and the quantity of mixed solution MS provided to the capillary chip CPC may be differently set. For example, when the button is pressed one time, the mixed solution MS by the quantity required for one time pre-treatment may be provided to the capillary chip CPC, or when the button is pressed two or three times, the mixed solution MS by the quantity required for one time pre-treatment may be provided to the capillary chip CPC.

As described above, the pre-treatment part PTP and the sensor part SSP are connected through the connector CNT, so that it is possible to simply mount or detach the capillary chip CPC of the sensor part SSP. That is, the capillary chip CPC of the sensor part SSP may be disposably used. The single-used capillary chip CPC may be discarded, and the new capillary chip CPC may be simply connected to the pre-treatment part PTP. Accordingly, the capillary chip CPC may be disposably used, and the pre-treatment part PTP may provide the mixed solution to the capillary chip CPC throughout plural times in accordance with the plurality of newly changed capillary chips CPC.

The calculation part CCP is connected to the sensor part SSP and the pre-treatment part PTP. The calculation part CCP controls the sensor part SSP and the pre-treatment part PTP, and calculates and digitizes information transmitted from the sensor part SSP, and outputs a result of the digitization.

The calculation part CCP may include a switch SW, through which a user is capable of manipulating the detecting process, a main board MB, which is connected with the switch SW, and controls the sensor part SSP and the pre-treatment part PTP and calculates a result value, and a display DSP, which is connected to the main board MB and displays a result value.

The switch SW is for the purpose of receiving a detection start or stop by the user, the number of times of the detection, and the like, and a form or a scheme thereof is not limited. In the exemplary embodiment of the present disclosure, the switch SW is called as the switch, but serves as an input means.

The main board MB is connected to the sensor part SSP and the pre-treatment part PTP, and controls the sensor part SSP and the pre-treatment part PTP. The main board MB performs various functions, such as controlling a degree of pressurization of the button of the pre-treatment part PTP or measuring a degree of color development by the photo sensor PI of the sensor part SSP according to an input of the user, or calculating a result value of the photo sensor PI, and thus obtains existence or non-existence of the target antigen AG, a concentration of the target antigen AG, or the like as a final result. Although not illustrated, a battery transferring power to the device may be connected to one side of the main board MB.

The display DSP displays a result value obtained by the main board MB. The display DSP may be provided in various forms, such as a quadrangle and a circle, and may adopt various schemes of display devices, such as an organic light emitting display device or a liquid crystal display device. The display DSP may display a result value obtained by calculating the existence or non-existence of the target antigen AG or the quantity of existing target antigen AG The display DSP may be omitted as necessary.

In the exemplary embodiment of the present disclosure, the calculated result value may also be output through an external device SP other than the display DSP. The calculated result value may also be output through the external device SP in a wired manner or a wireless manner using WiFi or Bluetooth. The external device SP may include various display devices, such as a smart phone, a personal portable terminal, and a smart watch.

A method of manufacturing the biosensor according to the exemplary embodiment of the present disclosure will be described below.

Referring to FIGS. 1 to 3, the method of manufacturing the biosensor according to the exemplary embodiment of the present disclosure includes an operation of manufacturing each of the sensor part SSP, the pre-treatment part PTP, and the calculation part CCP. An operation of manufacturing a sensor part SSP, an operation of manufacturing a pre-treatment part PTP, and an operation of manufacturing a calculation part CCP may be performed simultaneously or separately, and a manufacturing order is not limited. The sensor part SSP, the pre-treatment part PTP, and the calculation part CCP may be connected with one another later.

The sensor part SSP may be formed by forming a capillary chip CPC and disposing a photo sensor PI to be adjacent to the capillary chip CPC.

The operation of forming the capillary chip CPC includes preparing a capillary CP, forming a chromogenic enzyme-detection antibody HRP-DA on an inner wall of a first region R1 of the capillary CP, and forming a capture antibody CA on an inner wall of a second region R2 of the capillary CP. The chromogenic enzyme-detection antibody HRP-DA and the capture antibody CA may be formed as described below.

First, the capillary CP is prepared. Next, an internal surface of the capillary CP is treated and a hydroxyl (—OH) functional group is bonded to the internal surface. To this end, a piranha solution ($H_2SO_4:H_2O_2$ =7:3(v/v)) may be used. The prepared capillary CP is immersed in the piranha solution at 90° C. for 30 minutes. Then, an aldehyde silane ethanol solution of 0.1% is injected into the capillary CP and then the capillary CP is washed with ethanol after one hour. Next, the capillary CP is baked at 120° C. for 10 minutes, so that an aldehyde functional group for fixing the capture antibody CA is formed on the internal surface of the capillary CP. Next, the capture antibody CA is fixed onto the inner wall of the second region R2 by inserting the capture antibody CA into the capillary CP, in which the aldehyde functional group is formed on the internal surface of the capillary CP.

The capture antibody CA is fixed to the second region R2 of the capillary CP, a chromogenic enzyme-detection antibody HRP-DA solution is inserted into the first region R1 of the capillary CP, and then the chromogenic enzyme-detection antibody HRP-DA solution is inserted into a freeze-dryer, is cooled at 20 degrees below zero, and is freeze-dried, so that the chromogenic enzyme-detection antibody HRP-DA is formed in the first region R1.

The capillary chip CPC manufactured by the aforementioned method is connected to the separately manufactured pre-treatment part PTP and calculation part CCP later.

A method of detecting a target antigen by using the aforementioned biosensor will be described below.

Figure 5:
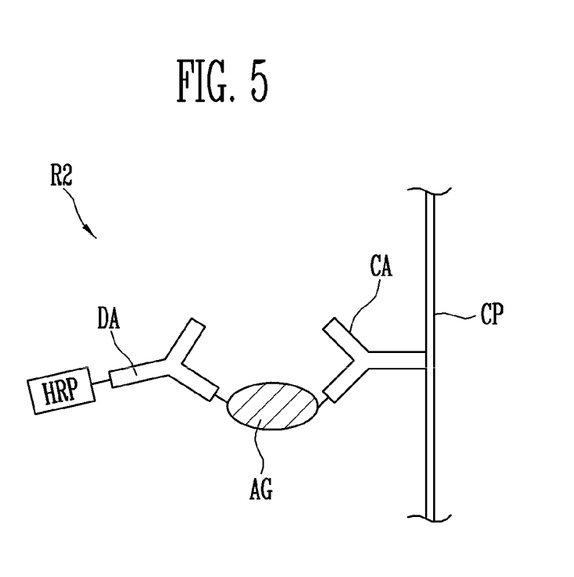
FIG. 5 is a diagram illustrating a principle of a target antigen detection in a capillary chip according to an exemplary embodiment of the present disclosure, and illustrates a principle of detecting a target antigen by using the sensor part of FIG. 3.

FIG. 5 is a diagram illustrating a principle of a target antigen AG detection in the capillary chip CPC according to the exemplary embodiment of the present disclosure, and illustrates a principle of detecting a target antigen AG by using the capillary chip CPC of FIG. 3.

Referring to FIGS. 3 and 5, a sample solution including a target antigen AG is provided to the biosensor according to the exemplary embodiment of the present disclosure. The sample solution is provided to the first opening OPN1 of the capillary chip CPC within the biosensor, and moves into the capillary chip CPC by capillary force.

The sample solution first arrives at the first region R1 within the capillary CP. The chromogenic enzyme-detection antibody HRP-DA is freeze-dried and disposed in the first region R1 of the inner wall of the capillary CP, and the chromogenic enzyme-detection antibody HRP-DA is dissolved in the sample solution.

When the target antigen AG is provided to the chromogenic enzyme-detection antibody HRP-DA, the target antigen AG acts as an antigen AG and may react with the chromogenic enzyme-detection antibody HRP-DA. The target antigen AG may be a complex of a "chromogenic enzyme-detection antibody-target antigen HRP-DA-AG" by the reaction. Then, the chromogenic enzyme-detection antibody-target antigen HRP-DA-AG may flow into the capillary CP along the capillary CP.

The chromogenic enzyme-detection antibody-target antigen HRP-DA-AG continuously flows into the capillary CP, that is, the second region R2, by capillary force.

The capture antibody CA is fixed to the second region R2, and the chromogenic enzyme-detection antibody-target antigen HRP-DA-AG reacts with the capture antibody CA, and particularly, the target antigen AG within the chromogenic enzyme-detection antibody-target antigen HRP-DA-AG performs a specific antibody-antigen reaction with the capture antibody CA. Accordingly, the chromogenic enzyme-detection antibody-target antigen HRP-DA-AG is fixed onto the inner wall of the capillary CP by the capture antibody CA.

Then, the mixed solution MS is provided into the capillary CP from the second opening OPN2 to the first opening OPN1. The non-reacted chromogenic enzyme-detection antibody-target antigen HRP-DA-AG is removed by the mixed solution MS, and the chromogenic enzyme-detection antibody-target antigen HRP-DA-AG fixed onto the inner wall of the capillary CP by the capture antibody CA is left. In this case, the substrate and the oxidizer (for example, hydrogen peroxide) are included in the mixed solution MS, so that the chromogenic enzyme HRP within the chromogenic enzyme-detection antibody-target antigen HRP-DA-AG fixed by the capture antibody CA acts as a catalyst. The chromogenic enzyme HRP accelerates an oxidization reaction of the substrate and the oxidizer, and thus, the substrate develops a color.

The photo sensor PI detects whether a color is developed within the capillary CP and a degree of color development, and transmits a result value of the detection to the calculation part CCP. The photo sensor PI may detect whether a color is developed within the capillary CP and a degree of color development by measuring light absorbance or transmittance when the color is developed.

Accordingly, the degree of color development by the reaction with the substrate is increased according to the quantity of target antigen AG; so that it is possible to determine existence and non-existence of the target antigen AG and calculate the content of target antigen AG according to the degree of color development.

According to the exemplary embodiment of the present disclosure, it is possible to detect whether the target antigen exists and the content of target antigen by a simple method by disposing materials having specificity, which are capable of detecting the target antigen, in the first region and the second region as described above. However, the kind of materials having specificity is not limited thereto.

Figure 6:
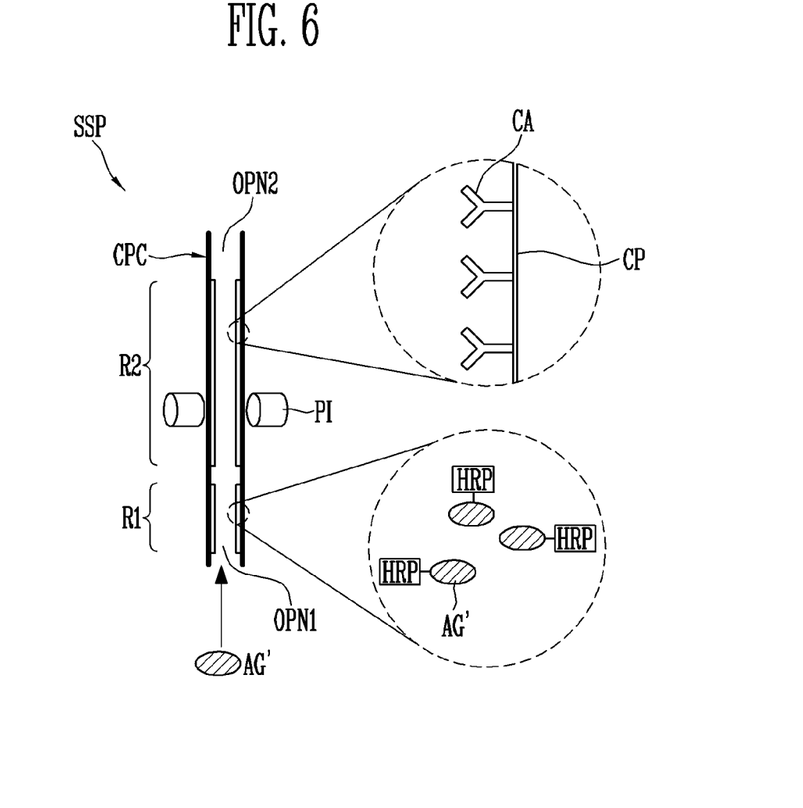
FIG. 6 is a diagram illustrating a capillary chip according to another exemplary embodiment of the present disclosure.
Figure 7:
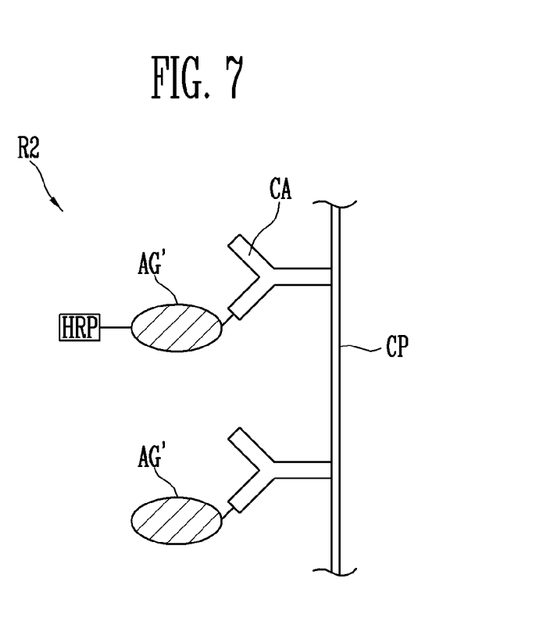
FIG. 7 is a diagram illustrating a principle of detecting a target antigen by using the capillary chip of FIG. 6.

FIG. 6 is a diagram illustrating a capillary chip according to another exemplary embodiment of the present disclosure, and FIG. 7 is a diagram illustrating a principle of detecting a target antigen by using the capillary chip of FIG. 6. In the exemplary embodiment below, for the convenience of description, different matters from those of the aforementioned exemplary embodiment will be mainly described, and overlapping contents will be omitted.

Referring to FIGS. 6 and 7, a chromogenic enzyme-target antigen HRP-AG' complex is provided to an inner wall corresponding to the first region R1 of the capillary CP, and a capture antibody CA is provided to the second region. The chromogenic enzyme-target antigen HRP-AG' complex may be selected from ones competitively reacting with the target antigen AG'. For example, an antigen connected to the chromogenic enzyme-target antigen HRP-AG' may be one competitively reacting with the target antigen AG', for example, the target antigen AG' itself desired to be detected, or may be one, which has antigen-antibody specificity to the capture antibody CA, such as the target antigen AG', and competitively reacts with the target antibody CA in the second region R2 together with the target antigen AG'.

The capture antibody CA provided to the second region R2 is provided as an antibody having antigen-antibody specificity to both the target antigen AG' and the chromogenic enzyme-the target antigen HRP-AG'.

A method of detecting the target antigen AG' by using the aforementioned biosensor will be described below.

Referring to FIGS. 6 and 7, a sample solution including the target antigen AG' is provided to the biosensor according to the exemplary embodiment of the present disclosure. The sample solution is provided to the first opening OPN1 of the capillary chip CPC within the biosensor, and moves into the capillary chip CPC by capillary force.

The sample solution first arrives at the first region R1 within the capillary CP. The chromogenic enzyme-target antigen HRP-AG' is freeze-dried and disposed in the first region R1 of the inner wall of the capillary CP, and the chromogenic enzyme-target antigen HRP-AG' is dissolved in the sample solution. Accordingly, the target antigen AG' and the chromogenic enzyme-target antigen HRP-AG' co-exist within the sample solution.

Then, the target antigen AG' and the chromogenic enzyme-target antigen HRP-AG' flow into the capillary CP along the capillary CP, and the target antigen AG' and the chromogenic enzyme-target antigen HRP-AG' continuously flows into the capillary CP, that is, the second region R2, by capillary force.

The capture antibody CA is fixed to the second region R2, and both the target antigen AG' and the chromogenic enzyme-target antigen HRP-AG' have antigen-antibody specificity to the capture antibody CA. Accordingly, the target antigen AG' and the chromogenic enzyme-target antigen HRP-AG' competitively react with the capture antibody CA and are bonded to the capture antibody CA. As a result, the target antigen AG' and the chromogenic enzyme-target antigen HRP-AG' reacted with the capture antibody CA are fixed onto the inner wall of the capillary CP by the capture antibody CA.

Then, the mixed solution MS is provided into the capillary CP from the second opening OPN2 to the first opening OPN1. A complex of the target antigen AG' and the chromogenic enzyme-target antigen HRP-AG', which is not reacted with the capture antibody CA by the mixed solution MS, is removed. The target antigen AG' reacting with the capture antibody CA and the chromogenic enzyme-target antigen HRP-AG' reacting with the capture antibody CA are fixed onto the inner wall of the capillary CP and left. In this case, a substrate and an oxidizer (for example, hydrogen peroxide) are included in the mixed solution MS, so that only a chromogenic enzyme (HRP) within the chromogenic enzyme-target antigen HRP-AG' in the target antigen AG' and the chromogenic enzyme-target antigen HRP-AG' fixed by the capture antibody CA acts as a catalyst. The chromogenic enzyme HRP accelerates an oxidization reaction of the substrate and the hydrogen peroxide, and thus, the substrate develops a color.

The photo sensor PI detects whether a color is developed within the capillary CP and a degree of color development, and transmits a result value of the detection to the calculation part CCP. The photo sensor PI may detect whether a color is developed within the capillary CP and a degree of color development by measuring light absorbance or transmittance when the color is developed.

Here, when the quantity of target antigen AG' is relatively large, the larger quantity of target antigen AG' is bonded with the target antibody CA in the competing reaction between the target antigen AG' and the target antibody CA of the chromogenic enzyme-target antigen HRP-AG', and as a result, the bonded quantity of chromogenic enzyme-target antigen HRP-AG' and the target antibody CA is decreased. This causes a decrease in a color development quantity of chromogenic enzyme HRP.

In contrast, when the quantity of target antigen AG' is relatively small, the smaller quantity of target antigen AG' is bonded with the target antibody CA in the competing reaction between the target antigen AG' and the target antibody CA of the chromogenic enzyme-target antigen HRP-AG', and as a result, the bonded quantity of chromogenic enzyme-target antigen HRP-AG' and the target antibody CA is increased. This causes an increase in a color development quantity of chromogenic enzyme HRP.

Accordingly, the degree of color development by the reaction with the substrate is increased according to the quantity of target antigen AG', so that it is possible to determine existence and non-existence of the target antigen AG' and calculate the content of target antigen AG' according to the degree of color development.

Figure 8:
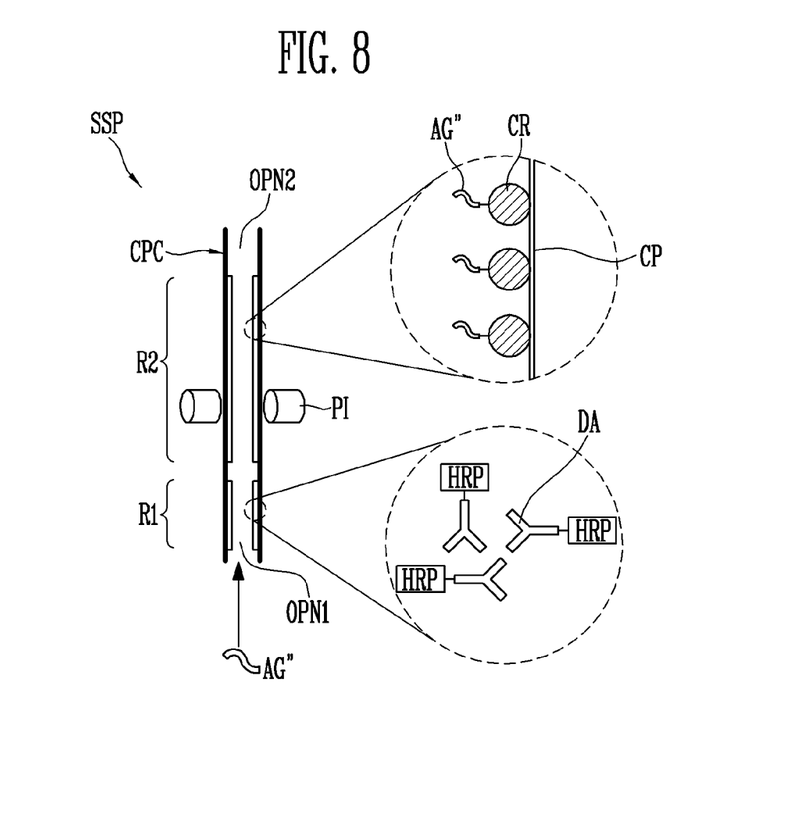
FIG. 8 is a diagram illustrating a capillary chip according to yet another exemplary embodiment of the present disclosure.
Figure 9:
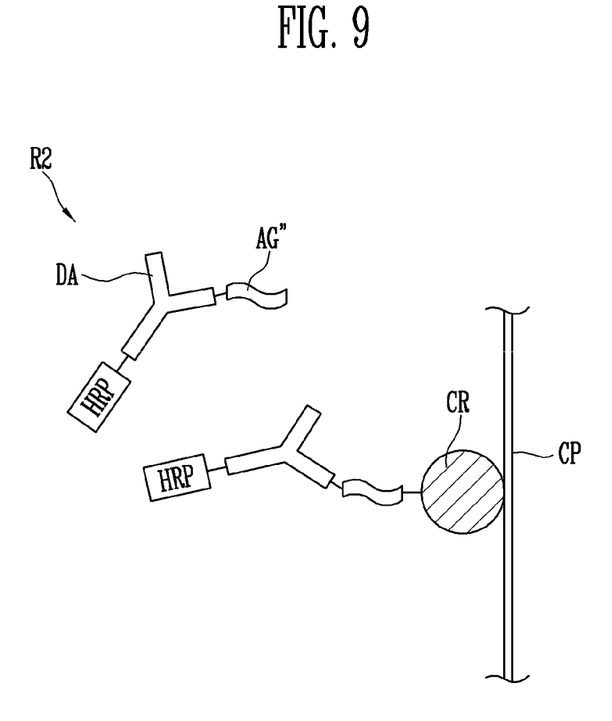
FIG. 9 is a diagram illustrating a principle of detecting a target antigen by using the capillary chip of FIG. 8.

FIG. 8 is a diagram illustrating a capillary chip according to yet another exemplary embodiment of the present disclosure, and FIG. 9 is a diagram illustrating a principle of detecting a target antigen AG by using the capillary chip of FIG. 8. The present exemplary embodiment may be carried out when a target antigen is a low polymer and a size of the target antigen is relatively small, and in the exemplary embodiment below, for the convenience of the description, different matters from those of the aforementioned exemplary embodiment will be mainly described, and overlapping contents will be omitted.

Referring to FIGS. 8 and 9, a chromogenic enzyme-detection antibody HRP-DA is provided on the inner wall corresponding to the first region R1 of the capillary CP.

The chromogenic enzyme-detection antibody HRP-DA may be a detection antibody DA, in which a chromogenic enzyme HRP is labelled. The detection antibody DA may be selected from antibodies having antigen-antibody specificity to a target antigen AG".

A complex of "target antigen-carrier AG"-CR" may be provided on the inner wall corresponding to the second region R2 of the capillary CP. The "target antigen-carrier AG"-CR" is one obtained by bonding a protein carrier CR to a target antigen AG" desired to be detected, and may be used when a size of the target antigen AG" is small. The carrier CR may be bovine serum albumin, casein, and the like. For example, when the target antigen AG" desired to be detected is cortisol, the target antigen-carrier AG"-CR complex may be a cortisol-bovine serum albumin complex.

A method of detecting the target antigen AG" by using the aforementioned biosensor will be described below.

Referring to FIGS. 8 and 9, a sample solution including the target antigen AG" is provided to the biosensor according to the exemplary embodiment of the present disclosure. The sample solution is provided to the first opening OPN1 of the capillary chip CPC within the biosensor, and moves into the capillary chip CPC by capillary force.

The sample solution first arrives at the first region R1 within the capillary CP. The chromogenic enzyme-detection antibody HRP-DA is freeze-dried and disposed in the first region R1 of the inner wall of the capillary CP, and the chromogenic enzyme-detection antibody HRP-DA is dissolved in the sample solution, and the chromogenic enzyme-detection antibody HRP-DA is bonded to the target antigen AG" through the antigen-antibody reaction. Accordingly, the chromogenic enzyme-detection antibody HRP-DA, which is bonded with the target antigen AG", and the chromogenic enzyme-detection antibody HRP-DA, which is not bonded with the target antigen AG", coexist in the sample solution.

Then, the chromogenic enzyme-detection antibody HRP-DA, which is bonded with the target antigen AG", and the chromogenic enzyme-detection antibody HRP-DA, which is not bonded with the target antigen AG", flow into the capillary CP along the capillary CP, and the chromogenic enzyme-detection antibody HRP-DA, which is bonded with the target antigen AG", and the chromogenic enzyme-detection antibody HRP-DA, which is not bonded with the target antigen AG", continuously flow into the capillary CP, that is, the second region R2, by capillary force.

The target antigen-carrier AG"-CR complex is fixed to the second region R2. The target antigen AG" within the target antigen-carrier AG"-CR complex has antigen-antibody specificity with the chromogenic enzyme-detection antibody HRP-DA, so that the target antigen AG" may be bonded with the chromogenic enzyme-detection antibody HRP-DA. Here, the chromogenic enzyme-detection antibody HRP-DA, which is already bonded with the target antigen AG", is not bonded with the target antigen-carrier AG"-CR complex, so that the chromogenic enzyme HRP complex, which is not bonded with the target antigen AG", is bonded with the target antigen-carrier AG"-CR complex.

The chromogenic enzyme HRP complex bonded with the target antigen-carrier AG"-CR complex is fixed onto the inner wall of the capillary CP.

Then, the mixed solution MS is provided into the capillary CP from the second opening OPN2 to the first opening OPN1. The chromogenic enzyme-detection antibody HRP-DA bonded with the target antigen AG" by the mixed solution MS is removed. The chromogenic enzyme HRP in the chromogenic enzyme-detection antibody HRP-DA, which is fixed onto and left on the inner wall of the capillary CP and is not bonded with the target antigen AG", acts as a catalyst in an oxidization of the substrate. That is, the substrate and the oxidizer (for example, hydrogen peroxide) are included in the mixed solution MS, so that the chromogenic enzyme HRP within the chromogenic enzyme-detection antibody HRP-DA fixed by the target antigen-carrier AG"-CR acts as a catalyst. The chromogenic enzyme HRP accelerates an oxidization reaction of the substrate and the hydrogen peroxide, and thus, the substrate develops a color.

The photo sensor PI detects whether a color is developed within the capillary CP and a degree of color development, and transmits a result value to a calculation part CCP. The photo sensor PI may detect whether a color is developed within the capillary CP and a degree of color development by measuring light absorbance or transmittance when the color is developed.

As described above, the degree of color development by the reaction with the substrate is changed according to the quantity of target antigen AG", so that it is possible to determine existence and non-existence of the target antigen AG" and calculate the content of target antigen AG" according to the degree of color development.

As described above, the biosensor according to the exemplary embodiment of the present disclosure is implemented by using a capillary chip by an Enzyme Linked Immunosorbent Assay (ELISA).

The existing ELISA method is performed on 96 well plates, so that a detection process is complex and it is substantially difficult to carry the well plates. However, according to the biosensor according to the exemplary embodiment of the present disclosure, the ELISA method is simply performed by a one-time pre-treatment within the capillary, so that it is possible to simply detect a specific biomarker compared to the related art.

The biosensor in the related art adopts a labelling method, in which a florescent material is labeled and used, and a method of detecting a material, such as gold nanoparticles, in a label free form, such as a surface Plasmon resonance. The method using the florescent material requires a florescent material, a wavelength for florescence excitation, and a complex optical device, such as a device reading the wavelength for florescence excitation. Accordingly, a biosensor using quantum dots has been developed, but a bonding property with a biomaterial is low, and there are many limits in surface-processing of the quantum dots. In addition, the existing method does not have the small quantity of color development, so that there is a disadvantage in that amplification is required and the like. Further, in a case of a generally used strip type biosensor, it is difficult to use a chromogenic enzyme and a structure of the strip type biosensor is complex, so that it is difficult to implement the ELISA. However, the biosensor according to the exemplary embodiment of the present disclosure may implement the ELISA by using a capillary, and suggest an apparatus and a method of detecting a biomarker by a simple method. Further, according to the exemplary embodiment of the present disclosure, a mixed solution usable plural times is provided to the container of the pre-treatment part, so that when only the capillary chip is replaced, it is possible to detect a target material by one-touch method over several times. Further, the biosensor according to the exemplary embodiment of the present disclosure has excellent accuracy and reproducibility.

In the biosensor according to the exemplary embodiment of the present disclosure, the sensor part, the pre-treatment part, and the calculation part may be longitudinally arranged in a predetermined direction and may have a shape of a note taking tool, so that it is possible to simply carry the biosensor. However, the shape of the biosensor is not limited thereto, and the biosensor may have other easily portable shapes.

According to the exemplary embodiment of the present disclosure, the biosensor may be used as a body disease factor detector used in a field diagnosis (Point Of Care (POC)). Particularly, the biosensor may be provided in a form of personal belongings, and thus a person may simply carry the biosensor and detect a physical disease, such as a chronic disease and influenza virus, and psychological disease, such as depression and stress, by easily analyzing a body fluid, such as blood, urine, and salvia. It is simple to use the biosensor according to the exemplary embodiment of the present disclosure, so that a user may easily check his/her health state. Further, the biosensor according to the exemplary embodiment of the present disclosure is disposed in a place, such as a silver town, a school, a daycare center, and a health center, so that it is possible to rapidly and easily recognize disease states of many people based on a body fluid, such as blood, urine, and salvia.

The biosensor according to the exemplary embodiment of the present disclosure may also be used for checking disease states of stock, such as cattle, pigs, chickens, and dugs, without limiting to the disease of the person. In this case, for the stock, the biosensor according to the exemplary embodiment of the present disclosure may be used as a detector for rapidly diagnosing diseases, such as avian influenza and a food-and-mouth disease, having strong contagiousness. In addition, the biosensor according to the exemplary embodiment of the present disclosure may check stress or depression states of stock, in addition to the disease of the stock, thereby improving productivity. For example, it is possible to check a stress or depression state, as well as a disease state, of a milk cow or a chicken, thereby improving milk production or egg production.

The technical spirit of the present disclosure have been described according to the exemplary embodiment in detail, but the exemplary embodiment has described herein for purposes of illustration and does not limit the present disclosure. Further, those skilled in the art will appreciate that various exemplary embodiments may be made within the technical spirit of the present disclosure.

What is claimed is:

1. A biosensor, comprising:
   a sensor part detecting a target material and having a cavity for accepting a capillary chip;
   a pre-treatment part connected to the sensor part and providing a mixed solution including a substrate to the sensor part; and
   a photo sensor provided in the sensor part detecting a color of the substrate,
   wherein the capillary chip comprises:
   a capillary haying a first region and a second region connected to the first region;
   a chromogenic enzymne-material provided onto an inner wall of the first region of the capillary, and
   a capture antibody fixed onto an inner wall of the second region of the capillary and having antigen-antibody specificity to the target material,
   where the chromogenic enzyme-material comprises:
   a chromogenic enzyme; and
   a material bonded to the chrormogenic enzyme and comprising at least one of a detection antibody and an antigen,
   wherein the photo sensor is adjacent to the second region of the capillary.

2. The biosensor of claim 1, wherein the capture antibody is competitively bonded with the target material and the chromogenic enzyme material.

3. The biosensor of claim 1, wherein the mixed solution includes any one of TMB(3,3',5,5'-Tetramethylbenzidine), and DAB(3,3'-Diaminobenzidine), ABTS(2,2'-azino-bis(3-ethylbenzothiazoline-6-sulphonic acid)) as a substrate, and the chromogenic enzyme is horseradish peroxidase.

4. The biosensor of claim 1, wherein the capillary tube is in straight shape with its longitudinal length covers from 10 mm to 100 mm, and wherein the capillary has a circle, an ellipse, or a polygon in a cross-sectional view, and has a width of 0.5 µm to 900 µm in a first direction and has a width of 0.5 µm to 900 µm in a second direction crossing the first direction.

5. The biosensor of claim 4, wherein the capillary is made of glass, crystal, or a transparent polymer, and the polymer includes at least one of polystyrene, polymethyl methacrylate, poly dimethyl siloxane, polycarbonate, and cyclic olefin copolymer.

6. The biosensor of claim 1, wherein the photo sensor detects transmittance according to whether the substrate develops a color.

7. The biosensor of claim 1, wherein the capillary chip is mountable to and detachable from the pre-treatment part.

8. The biosensor of claim 7, wherein the target material comprises a target antigen.

9. The biosensor of claim 1, wherein the pre-treatment part includes the mixed solution, a container accommodating the mixed solution, and a mixed solution providing means providing the mixed solution to the capillary chip, and
   the mixed solution providing means is a piston.

10. The biosensor of claim 1, further comprising:
    a calculation part connected to the sensor part and the pre-treatment part, the calculation part comprising:
    a switch manipulating a detecting process and serving as an input; and
    a main board connected with the switch and controlling the senor part and the pre-treatment part, the main board calculating a result value.

11. The biosensor of claim 10, wherein the calculation part includes a display displaying the result value obtained by the main board.

12. The biosensor of claim 10, wherein the calculation part outputs the result value to a wirelessly connected external device.

13. A biosensor comprising:
    sensor part detecting a target material and having a cavity for accepting a capillary chip;
    a pre-treatment part connected to the sensor part and providing a mixed solution including a substrate to the sensor part; and
    a photo sensor provided in the sensor part and detecting a color of the substrate, wherein the capillary chip comprising:
    a capillary having a first region and a second region connected to the first region;
    a chromogenic enzyme-detection antibody provided onto an inner wall of the first region of the capillary and spaced apart from the second region of the capillary; and
    a target material-carrier complex provided on an inner wall of the second region of the capillary and spaced apart from the first region of the capillary,
    wherein the photo sensor is adjacent to the second region of the capillary.

14. The biosensor of claim 13, wherein the carrier is bovine serum albumin or casein.

* * * * *